United States Patent [19]

Scheller

[11] 4,301,141
[45] Nov. 17, 1981

[54] STRONG FOAMING TOOTHPASTE
[75] Inventor: Hans U. Scheller, Eislingen, Fed. Rep. of Germany
[73] Assignee: Wurttembergische Parfumerie-Fabrik GmbH, Eislingen, Fed. Rep. of Germany
[21] Appl. No.: 188,897
[22] Filed: Sep. 19, 1980
[30] Foreign Application Priority Data Mar. 26, 1980 [DE] Fed. Rep. of Germany ....... 3011618

[51] Int. Cl.³ .......................... A61K 7/16; A61K 7/26
[52] U.S. Cl. .......................................... 424/7; 424/49
[58] Field of Search .................... 424/49–58, 424/7, 359, 360

[56] References Cited

U.S. PATENT DOCUMENTS 3,839,590 10/1974 Battista ................................. 424/49
3,981,989 9/1976 Suganuma et al. .................... 424/50
4,058,595 11/1977 Colodney .............................. 424/50
4,058,596 11/1977 Nachtigal .............................. 424/50
4,223,003 9/1980 Scheller ................................. 424/7
4,243,655 1/1981 Gunther ............................. 424/49 X

FOREIGN PATENT DOCUMENTS 2747092 4/1979 Fed. Rep. of Germany .......... 424/7

*Primary Examiner*—Shep K. Rose
*Attorney, Agent, or Firm*—Merriam, Marshall & Bicknell

[57] ABSTRACT

An improved strong foaming toothpaste containing gelatin, a gelatinous eggwhite product or a mixture thereof and at least one surfactant. The gelatin or gelatinous eggwhite product makes it possible to reduce the surfactant content, thereby providing a toothpaste which avoids the adverse effects a high content of surfactant has on the mouth mucous membrane.

About 1 to 2.5% by weight of surfactant and 1 to 10% by weight of gelatin, a gelatinous eggwhite product, or mixture thereof, can be used in the toothpaste.

10 Claims, No Drawings

STRONG FOAMING TOOTHPASTE

This invention relates to toothpaste having strong foaming ability. More particularly, this invention is concerned with a strong foaming toothpaste containing gelatin, a gelatinous eggwhite product, or mixture thereof, and a surfactant foaming agent.

Toothpastes with strong foaming ability are preferred by many customers since the thick foam gives a feeling of intensive cleaning. Also desired by customers are toothpastes which pass through a color change during brushing since the color change provides an observable or optical cleaning control. German published patent application No. 2,747,092 discloses a strong foaming toothpaste with an optical cleaning control capability. The thick foam can substantially mask or hide the coloring agent so that color change is as readily observed during use of the toothpaste as desired.

Previously, toothpastes having a strong foaming ability had to contain a high content of foaming surfactants. According to German published patent application No. 2,747,092, a surfactant content of above 2.5% is necessary to achieve minimal optical cleaning control with brushing. It has been previously known that a higher concentration of surfactant or wetting agent adversely affects toothpaste flavoring characteristics. This is especially true of toothpastes in which the surfactant is soap. Furthermore, it has been known that toothpastes with larger amounts of surfactant loosen the epithelia intercellular structure of the mouth mucous membrane and that the mechanical abrasive action of the toothbrush enhances the resulting scaling-off action. Many literature references report the occurence of epithelized lesions caused by the surfactants.

One of the purposes of this invention is to provide a novel toothpaste with strong foaming ability containing one or more surfactants which minimizes or eliminates the above discussed disadvantages of toothpastes having a high surfactant content.

According to the present invention, it has been found that a toothpaste with strong foaming ability is obtained by including gelatin, a gelatinous eggwhite product or a mixture thereof, in the toothpaste. Generally, the amount of gelatin, gelatinous eggwhite product or mixture thereof, included is in the range of about 1 to 10%, and desirably 2 to 7%, by weight of the toothpaste.

The inclusion in a toothpaste of gelatin, a gelatinous eggwhite product, or a mixture thereof, makes it possible to significantly reduce the toothpaste surfactant content and still obtain high foaming ability. The surfactant content of the toothpaste, for example, can be about 1 to 2.5% by weight, and desirably is 1.5 to 2% by weight.

It is surprising to find that the surfactant content of a high foaming toothpaste can be reduced, and a portion of the surfactant content replaced, by gelatin, a gelatinous eggwhite product or a mixture thereof. This is because it was known that surfactants and gelatin or a gelatinous eggwhite product form reaction products which contain the characteristics of the initial components at a much lower level or completely lack such characteristics. In particular, the normal characteristic of the surfactants to wet and foam was known to be reduced by the addition of protein substances. Accordingly, it was not expected that the combination of surfactants and gelatin, a gelatinous eggwhite product or mixture thereof, in toothpaste nonetheless would produce a strong foaming product.

The finding of the invention is of particular importance in an optical brushing control toothpaste, such as disclosed in German published patent application No. 2,747,092. Such a toothpaste was only possible with a surfactant content above 2.5% even though for medical reasons and taste it was highly desirable to have a surfactant content of 2% or less, and desirably not higher than 1%.

The gelatin or gelatinous eggwhite product, or mixture thereof, used in the toothpaste, can be obtained from any foodstuff, provided the gelatin product has acceptable chemical and physiological qualities for use in the toothpaste. Gelatin, gelatin hydrolyzates or collagen hydrolyzates are specifically useful.

Particularly suitable are gelatins which are soluble in cold water and, in addition, have a high foaming ability of their own. Acid extracted gelatin from the thick skin of hogs has such qualities. Other preferred products are gelatin types copper and copper A/B, as well as the gelatin hydrolyzate CF, available from the German gelatin factory of Stoess and Co., GmbH, Eberbach-/Baden. These gelatins have a weak viscosity and gelling ability, low pH, are soluble in cold water and have a relatively strong foaming ability of their own.

It has been suggested previously in the literature to thicken toothpastes with eggwhites, in particular eggwhite gelatin. This has not been done, however, because of considerable technical difficulties. Conventional gelatin must be dissolved hot and this delays production. Furthermore, such a toothpaste is unstable with respect to temperature and consequently is unsuitable for use. The amounts of gelatin added according to the invention are substantially less than those needed for thickening the toothpaste. The amounts of gelatin added do not influence the toothpaste viscosity, or else influence it to such a small extent that no effect is observed.

Surprisingly, the gelatin added to the toothpaste of the invention reduces the adverse action of the surfactant on the mouth mucous membrane. Furthermore, the undesirable influence of the surfactant on the toothpaste taste is also reduced by the inclusion of gelatin. In addition, the oral dryness subjectively felt relatively often due to the high surfactant content of the prior art toothpaste is no longer observed in the toothpaste provided by the invention.

In an optical cleaning control toothpaste, such as is disclosed in German published patent application No. 2,747,092, it is easily possible according to the invention to lower the surfactant content to about 1.5 to 2% by weight while obtaining the same decoloring effect by means of strong foam development.

Representative of highly suitable surfactants which can be used in a toothpaste according to the invention are water soluble salts of higher alkyl sulfates such as sodium lauryl sulfate, aliphatic acylamides; saturated monoamino fatty acids and preferably sodium-N-lauroyl sarcosine; taurine fatty acid amides; salts of sulfonated monoglycerides of higher fatty acids; fatty acid esters of isethionic acid and its salts; nonionic surfactants such as alkylene oxide condensates with a fatty alcohol and a mono or polyvalent amine; sugar esters; long chain amine oxides; ampholytic oxides such as betaine or long chain alkyl amino carboxylic acids; and cationic surfactants such as quaternary ammonium compounds. It should be understood, however, that the choice of surfactants is not critical to the invention since so many different surfactants can be used.

The surfactants can be used singly or as a mixture and can be present in the toothpaste in an amount in the range of 1 to 2.5%, desirably 1.5 to 2%, by weight. Lower concentrations generally do not provide a desirably high foaming ability and higher concentrations are undesirable for reasons given above.

The toothpaste can include about 1 to 10%, and preferably 2 to 7%, by weight of gelatin, a gelatinous eggwhite product, or a mixture thereof. Lower amounts do not contribute sufficiently to foam formation so that the surfactant would have to be increased unnecessarily and undesirably. Amounts greater than 10% are generally not used because then a noticeable influence on the viscosity can be observed and this can lead to undesirable effects because of the temperature instability of the gelatins.

The toothpaste according to the invention can contain the usual additives and components. Moisture retaining materials such as glycerin, polyglycols of low molecular weight, and sugar alcohols such as sorbitol, mannitol and xylitol can be included. Thickening agents preferably used are the alkali metal salts of carboxymethyl cellulose and in particular sodium carboxymethylcellulose; hydroxyalkylcellulose and in particular hydroxyethylcellulose; vegetable gums such as tragacanth, gum arabic, caraya gum and Irish moss; synthetic polyelectrolytes and, possibly, inorganic thickening substances such as colloidal magnesium aluminum silicates. Especially preferred is fumed silica made from $SiCl_4$. Furthermore, the toothpaste of the invention can contain calcium carbonate and/or dicalcium phosphate as well as the usual flavoring and perfume agents, stabilizing substances et cet.

Preferred embodiments of the invention contain fluorine compounds in such an amount that the concentration of fluorine is between 0.01 to 1%, and desirably 0.1 to 0.5%, by weight.

Suitable fluorine compounds are, in particular, the various salts of monofluorophosphoric acid, as well as the various fluorides containing the fluorine in ionic form, in particular, the alkali metal fluorides such as sodium fluoride, lithium fluoride, and potassium fluoride; ammonium fluoride, tin fluoride, manganese fluoride, zirconium fluoride and aluminum fluoride, as well as mixtures thereof, or addition products of these fluorides with other fluorine compounds, e.g., potassium manganese fluoride or sodium manganese fluoride. Further fluorides usable according to the invention are zinc fluoride, germanium fluoride, palladium fluoride, titanium fluoride, alkali fluorine-zirconates, and fluorine sulphates. Also, the known additive products of long chain amino acids and hydrogen fluoride, and particularly monethanol amino hydrofluoride and methyltriethylammoniumfluoride, can be used.

A toothpaste according to the invention further can contain substances which loosen the tartar deposits, such as phosphonic acids, as well as bis-biguanides like chlorohexidine, fluorohexidine and alexidine, as well as their water soluble salts.

A toothpaste with optical brushing control according to German published patent application No. 2,747,092 can contain all the components, and is preferably manufactured according to the method, mentioned therein with one single exception that the surfactant content is lowered and instead gelatin, a gelatinous eggwhite product, or mixture thereof, is added according to the invention in place of the surfactant portion which has been eliminated.

A particularly suitable toothpaste, according to the invention, having optical cleaning control contains a sufficient amount of foam coloring agent so that at the beginning of brushing of the teeth a colored foam is produced which after at least 20 seconds of brushing shows foam decolorization by a brightness difference $\Delta L$ in the range of about 10 to 30, and desirably 15 to 25, with the brightness $L=0$ for black and $L=100$ for white, and the foam is subsequently decolored to white or a faintly colored condition.

The following examples illustrate new toothpaste compositions produced according to the invention.

EXAMPLE 1

A toothpaste was prepared by conventional manufacturing methods using a gelatin of conventional food quality (gelatin Cu of the German Gelatinefabriken Stoess & Co., GmbH, Eberbach/Baden):

| Substance | Amount in Percent/Weight |
| --- | --- |
| Carboxymethylcellulose | 0.8 |
| Calcium carbonate | 25.0 |
| Sodium lauryl sulfate | 2.0 |
| Sodium myristoyl taurate | 0.5 |
| Gelatin Cu | 3.0 |
| Glycerine 86% or sorbitol | 12.0 |
| Sodium salt of p-hydroxybenzoic acid methyl ester | 0.2 |
| Fumed silica (from $SiCl_4$) | 2.0 |
| Flavoring and perfume materials | 2.0 |
| L-Blue No. 3 (CI No. 42 051) | 0.006 |
| Water, demineralized | add to 100.0 |

The effect of the toothpaste according to the invention with respect to decoloring of the formed foam has been tested on five persons with an electric toothbrush (AEG-Princess). Each time a strand of 2 cm paste (corresponding to 0.5 g) was put on the moistened toothbrush and the brushing procedure was continued until the foam, which was clearly blue at the beginning, became white, or, within a reasonable brushing period, no longer showed any change in color. The results obtained were as follows:

|  | Time to Become White |
| --- | --- |
| 1. test person | after 100 sec. |
| 2. test person | after 100 sec. |
| 3. test person | after 80 sec. |
| 4. test person | after 90 sec. |
| 5. test person | after 80 sec. |
| average duration = 90 sec. | |

In comparison, a toothpaste according to German published patent application No. 2,747,092 having the following composition was tested:

| Substance | Amount in Percent/Weight |
| --- | --- |
| Carboxymethylcellulose | 1.0 |
| Calcium carbonate | 25.0 |
| Sodium lauryl sulfate | 3.0 |
| Sodium myristoyl taurate | 0.5 |
| Glycerine 86% or sorbitol | 12.0 |
| Sodium salt of p-hydroxybenzoic acid methyl ester | 0.2 |
| Fumed silica (from $SiCl_4$) | 2.0 |
| Flavoring and perfume materials | 2.0 |
| L-Blue No. 3 (CI No. 42 051) | 0.006 |

| Substance | Amount in Percent/Weight |
| --- | --- |
| Water, demineralized | add to 100 |

This toothpaste contained 3.5 percent/weight of surfactants.

Brushing tests were carried out as described above and the following results obtained:

| | Time to Become White |
| --- | --- |
| 1. test person | after 110 sec. |
| 2. test person | after 80 sec. |
| 3. test person | after 90 sec. |
| 4. test person | after 110 sec. |
| 5. test person | after 90 sec. |
| average duration = 96 sec. | |

These tests unmistakably reveal that the total surfactant content as compared to the known composition, could be reduced by 1 percent/weight and approximately identical results nevertheless obtained.

EXAMPLE 2

A toothpaste was prepared from the following ingredients using acid extracted gelatin from hog skin:

| Substance | Amount in Percent/Weight |
| --- | --- |
| Carboxymethylcellulose | 1.0 |
| Calcium carbonate | 25.0 |
| Sodium lauryl sulfate | 1.5 |
| Sodium myristoyl taurate | 0.05 |
| Glycerine 86% or sorbitol | 12.0 |
| Sodium salt of p-hydroxybenzoic acid methyl ester | 0.2 |
| Fumed silica (from SiCl4) | 2.0 |
| Flavoring and perfume materials | 2.0 |
| Gelatin hydrolyzate | 3.5 |
| L-Blue No. 3 (CI No. 42 051) | 0.006 |
| Water, demineralized | add to 100.00 |

The brushing tests, conducted as described in Example 1, gave the following results:

| | Time To Become White |
| --- | --- |
| 1. test person | after 120 sec. |
| 2. test person | after 100 sec. |
| 3. test person | after 80 sec. |
| 4. test person | after 90 sec. |
| 5. test person | after 90 sec. |
| average duration = 96 sec. | |

As compared to the known composition (Example 1), the surfactant content of this toothpaste has been lowered to 2.0% and, despite this, results completely comparable to those with the prior art toothpaste (Example 1) composition of much higher surfactant content, were obtained.

EXAMPLE 3

A strongly foaming toothpaste was prepared according to the invention containing sodium monofluorophosphate.

| Substance | Amount in Percent/Weight |
| --- | --- |
| Fumed silica (from SiCl4) | 3.0 |
| Carboxymethylcellulose | 1.0 |
| Dicalcium phosphate | 30.0 |
| Sodium lauryl sulfate | 2.0 |
| Sodium myristoyl taurate | 0.5 |
| Glycerine 86% or sorbitol or propylene glycol | 14.0 |
| Sodium monofluorophosphate | 0.76 |
| Sodium salt of p-hydroxybenzoic acid methyl ester | 0.2 |
| Gelatin Cu | 3.0 |
| Flavoring and perfume materials | 2.0 |
| Water, demineralized | 100.0 |

EXAMPLE 4

A medically recommended strongly foaming fluorine containing toothpaste was prepared with a 2% by weight of surfactants using the following ingredients:

| Substance | Amount in Percent/Weight |
| --- | --- |
| Fumed silica (from SiCl4) | 3.0 |
| Carboxymethylcellulose | 1.0 |
| Dicalcium phosphate | 30.0 |
| Sodium lauryl sulfate | 1.7 |
| Sodium myristoyl taurate | 0.3 |
| Gelatin hydrolyzate | 4.0 |
| Glycerine 86% or sorbitol | 12.0 |
| Sodium salt of p-hydroxybenzoic acid methyl ester | 0.2 |
| Flavoring and perfume materials | 2.0 |
| Sodium monofluorophosphate | 0.76 |
| Water, demineralized | add to 100.0 |

The gelatine hydrolyzate is a cold-water soluble, strongly foaming product of the German Gelatinefabriken Stoess & Co., GmbH, Eberbach (Gelatine hydrolyzate CF).

The foregoing detailed description has been given for clearness of understanding only, and no unnecessary limitations should be understood therefrom, as modifications will be obvious to those skilled in the art.

What is claimed is:

1. In a toothpaste with high foaming ability containing at least one surfactant, the improvement comprising including in the toothpaste about 1 to 10% by weight of a gelatin soluble in cold water, a gelatinous eggwhite product soluble in cold water, or a mixture thereof, about 1 to 2.5% by weight of surfactant, and a sufficient amount of a foam coloring agent for optical cleaning control so that at the beginning of brushing of the teeth a colored foam is produced which after at least 20 seconds of brushing shows foam decolorization by a brightness difference $\Delta L$ in the range of about 10 to 30 with the brightness $L=0$ for black and $L=100$ for white, and the foam is subsequently decolored to white or a faintly colored condition.

2. In a toothpaste with high foaming ability containing at least one surfactant, the improvement comprising including in the toothpaste about 1 to 10% by weight of a cold water soluble gelatin hydrolyzate alone or in admixture with a gelatinous eggwhite product soluble in cold water, about 1 to 2.5% by weight of surfactant, and a sufficient amount of a foam coloring agent for optical cleaning control so that at the beginning of brushing of the teeth a colored foam is produced which after at least 20 seconds of brushing shows foam decolorization by a brightness difference $\Delta L$ in the range of about 10 to 30 with the brightness $L=0$ for black and $L=100$ for white, and the foam is subsequently decolored to white or a faintly colored condition.

3. An improved toothpaste according to claim 2 in which the surfactant content is about 1 to 2% by weight.

4. An improved toothpaste according to claim 2 containing about 2 to 7% by weight of gelatin hydrolyzate alone or in admixture with a gelatinous eggwhite product.

5. An improved toothpaste according to claim 2 containing about 2 to 7% by weight of gelatin hydrolyzate alone or in admixture with a gelatinous eggwhite product, and a surfactant content of about 1 to 2% by weight.

6. An improved toothpaste according to claim 2 in which the $\Delta L$ after at least 20 seconds of brushing is about 15 to 25.

7. An improved toothpaste according to claim 1 1 in which the surfactant content is about 1 to 2% by weight.

8. An improved toothpaste according to claim 1 containing about 2 to 7% by weight of gelatin, a gelatinous eggwhite product or a mixture thereof.

9. An improved toothpaste according to claim 1 containing about 2 to 7% by weight of gelatin, a gelatinous eggwhite product, or a mixture thereof, and a surfactant content of about 1 to 2% by weight.

10. An improved toothpaste according to claim 1 in which the $\Delta L$ after at least 20 seconds of brushing is about 15 to 25.

* * * * *